United States Patent [19]
Moseley

[11] Patent Number: 5,138,663
[45] Date of Patent: Aug. 11, 1992

[54] METHOD AND APPARATUS FOR PERFORMING NOISE CANCELLING AND HEADPHONING

[75] Inventor: William T. Moseley, Shreveport, La.

[73] Assignee: MNC, Inc., Shreveport, La.

[21] Appl. No.: 600,185

[22] Filed: Oct. 19, 1990

Related U.S. Application Data

[63] Continuation-in-part of Ser. No. 558,342, Jul. 27, 1990, which is a continuation-in-part of Ser. No. 532,323, Jul. 10, 1990, which is a continuation-in-part of Ser. No. 392,264, Aug. 10, 1989, Pat. No. 5,001,763.

[51] Int. Cl.$^5$ .............................................. G10K 11/16
[52] U.S. Cl. .......................................... 381/71; 381/72
[58] Field of Search .......................... 381/71, 72, 158; 181/151, 166, 198

[56] References Cited

U.S. PATENT DOCUMENTS

| | | | |
|---|---|---|---|
| 1,655,267 | 1/1928 | Hahnemann et al. | 181/146 |
| 4,284,844 | 8/1981 | Belles | 181/151 |
| 4,439,644 | 3/1984 | Bruney, III | 181/151 |

Primary Examiner—Forester W. Isen
Attorney, Agent, or Firm—Cushman, Darby & Cushman

[57] ABSTRACT

A device for performing electroacoustic functions including noise cancellation, communication interface, and headphone functions. The device includes a composite transducer which is connected to a control unit. The composite transducer, which is adapted for use with the human ear, includes: at least one input transducer for converting acoustic waves into electrical signals, and an output transducer facing the ear for converting electrical signals into acoustic waves. The transducers are oriented to be substantially coplanar to each other. The control unit includes circuitry for driving the output transducer based on electrical signals from the input transducer(s) with an amplitude and phase to perform the noise cancellation, sound filtering, communication interface, and headphone functions. The composite transducer includes a multiple baffle acoustic diffuser which performs frequency filtering, allows sound origin selection, and lengthens the paths of selected sounds entering the composite transducer.

14 Claims, 7 Drawing Sheets

METHOD AND APPARATUS FOR PERFORMING NOISE CANCELLING AND HEADPHONING

CROSS REFERENCE TO RELATED APPLICATIONS

This application is a continuation-in-part of Application Ser. No. 07/558,342, filed July 27, 1990, which is a continuation-in-part of Application Ser. No. 07/532,323, filed July 10, 1990, the subject matter of which is incorporated herein by reference and which is itself a continuation-in-part of Application Ser. No. 07/392,264 filed Aug. 10, 1989, now U.S. Pat. No. 5,001,763.

FIELD OF THE INVENTION

This invention relates to electroacoustic devices for performing noise cancellation, communication interfacing, sound filtering, and headphone functions for the human ear.

DESCRIPTION OF RELATED ART

In performing sound cancellation, an incoming noise (a sound wave) is sensed and an opposing sound wave is generated which has the same amplitude and frequency but which is 180° out of phase with the incoming wave. The result is that the incoming wave is cancelled when it meets the opposing wave.

Sensing of the incoming wave is typically performed by an input transducer which converts the incoming noise into a corresponding electrical signal. The electrical signal is then typically phase shifted by 180° (inverted) by electrical circuitry. An output transducer then typically converts the phase shifted electrical signal into the opposing sound wave.

Various prior art headphone configurations have been developed for positioning these sound cancellation input and output transducers in relation to the ear.

U.S. Pat. No. 4,455,675 issued to Bose et al., for example, discloses a headphone which uses a donut-like shaped sound attenuating cushion to form a cavity in a volume bounded by the cushion, the user's ear canal, and the headphone. This cavity contains one output transducer and one input transducer. The input transducer is located facing the ear between the output transducer diaphragm and the entrance to the ear canal. The cushion is made from a material which attenuates middle range frequencies around 2kHz so that the cavity is somewhat acoustically isolated from the outside environment.

U.S. Pat. No. 4,644,581 issued to Sapiejewski also discloses a headphone in which a donut-shaped cushion made of a damping material seals with a user's ear pinna to create a cavity continuous with the ear canal. In Sapiejewski, however, an additional piece of damping material is used. This additional piece of damping material, which attenuates high frequency resonances, is positioned to further separate the cavity into a headphone cavity containing the transducers and an ear canal cavity. Sapiejewski shows the input transducer and the output transducer oriented perpendicular to each other inside the headphone cavity. The pickup surface of the input transducer does not face the ear cavity.

BACKGROUND OF THE INVENTION

The invention disclosed in Application Ser. No. 07/532,323 involves a composite transducer assembly with an input transducer and an output transducer. The input transducer is oriented facing out from the ear and toward the source of noise to be cancelled. The output transducer, on the other had, is oriented to face in the opposite direction toward the ear canal of the user.

If ideal transducers were available with flat amplitude versus frequency response and with identical phase response versus each other, which instantaneously converted sound waves into electrical signals and visa versa, and if the source signal arrived at the ear and at the input transducer at exactly the same time, and if the circuitry to invert the input electrical signal from the input transducer did not introduce a delay or the ballistics of the transducers did not introduce a delay, all acoustic energy entering the ear canal would be canceled by the opposing wave output from the output transducer.

Transducers, however, are not ideal. Specifically, input transducers such as small electret microphones have a different phase response from output transducers such as small headphone type speakers. Similarly, output transducers such as a small headphone type speakers have a characteristic roll-off in output amplitude versus frequency of the input electrical signal. This roll-off occurs at low frequencies.

More specifically, electret microphones have a reasonably flat amplitude versus frequency response over a wide range of the audio frequency spectrum (eg. ±3Db 20Hz–16KHz). Due to the way an electret microphone is made, several problems exist in making it the ideal input device for use with an output transducer such as a small headphone type speaker.

The two most important differences between an electret microphone and a speaker are their different phase and amplitude versus frequency responses. An electret microphone element is basically a variable capacitor with a FET semiconductor to convert the changing capacitance into an electrical signal. As sound pressure is applied to the input diaphragm of the electret microphone, it changes capacitance in relation to the varying pressure. This capacitance variation is converted into a corresponding electrical signal by the FET semiconductor. The FET requires a DC voltage to operate. The output of the FET is then presented to the input of a preamplifier for further amplification to raise the signal to a usable level. The phase of the signal output by the FET may not be the same as the phase of the signal that would be output by an output transducer such as a small headphone type speaker. This different phase relationships of the input transducer and the output transducer produce an error in the desired exact 180° phase shift desired between the input and output transducers. This error then does not allow complete cancellation of the source signal that reaches the ear canal.

Another problem that causes a phase shift difference between the input transducer and the output transducer is the use of a coupling capacitor between the electret microphone and its preamplifier. With current low cost semiconductors there is a maximum supply voltage that can be applied to the integrated circuit (IC) preamplifier. Typically this is ±18VDC maximum.

This maximum supply voltage also dictates the maximum output signal that can be generated by the IC. With a supply voltage of ±18VDC, the maximum signal swing that could be generated would be 36 volts. To amplify the signal from the input transducer to a usable level, amplification factors or gains of 500 to 1000 are needed. Since the electret microphone requires a DC voltage in the range of 2 to 10 volts to operate, the preamplifier IC would need to produce an output signal of 1000 to 2000 volts. This is of course not possible, so the DC supply voltage for the electret microphone can not be presented to the preamplifier for amplification. A capacitor is therefore used to block the DC voltage from the input to the preamplifier. This capacitor introduces a phase shift in the signal, thereby adding an error between the input transducer and the output transducer phase coherence. Some ICs can be offset by a given amount which corrects this problem, but the phase and the frequency response of the preamplifier IC working at the required gains is then altered resulting in another source of phase error. If an IC was capable of offsetting the supply voltage to the input transducer and amplifying the signal to the required level with flat amplitude and phase versus frequency response, it would be the ideal device for a preamplifier.

The output transducer also has problems that introduce error in the desired processed signal output. A output transducer such as a speaker does not have a flat amplitude versus frequency response over the same audio spectrum as the input transducer. This results in an error in the amplitude summation of the original source signal and the signal output by the output transducer. If the signals are not the exact same amplitude and 180° out of phase, complete cancellation is not achieved. Output transducers such as small headphone type speakers roll-off at the lower frequencies. This does not allow complete cancellation of all frequencies. The low frequency response of the output transducer can be increased with the use of an enclosure to the back side of the output transducer much like a stereo loudspeaker uses to extend its low frequency response. This, however, does not lend itself to producing the composite transducer. The enclosure has to have a certain internal volume of air and would be bulky and heavy. The intent of the composite transducer is to be as small and light weight as possible It is possible, however, for an enclosure to be put on the composite transducer which extends the low frequency response using materials such as plastic for weight reasons. If an enclosure is used to extend the response, it is still necessary for the original source signal to reach the input transducer at the same time as it reaches the ear canal.

Accordingly, when the invention disclosed in the parent Application Ser. No. 07/532,323 is realized using real input and output transducers, the less than ideal characteristics of the transducers affect the noise cancellation as the frequency of the input noise changes. If the gain and phase of the amplifier amplifying the output from the input transducer is changed so that the low frequency noise is cancelled, an incorrect electrical signal will then drive the speaker for high frequency noise. The low frequency components of the noise would be better cancelled but the high frequency components would not.

Accordingly, when non ideal transducers are used in the composite transducer assembly of the present invention, residual uncanceled noise is left in the ear canal.

SUMMARY OF THE INVENTION

This invention therefore adds a second input transducer to the composite transducer disclosed in Applicant Ser. No. 07/532,323. The second input transducer is oriented in the opposite direction from the first input transducer. The second transducer lies in the plane of the input and output transducers of the application Ser. No. 07/532,323, but faces the ear canal cavity so that it detects the residual uncanceled noise present inside the ear canal cavity. After detecting the residual noise, the second input transducer outputs a signal to the electrical circuitry in the control unit of the invention so that an opposing sound wave 180° out of phase with the residual noise will be input into the ear canal cavity by the output transducer.

Due to the principles explained in the parent applications by which the pickup surfaces of the first input transducer and the output transducer are located in the same plane, so also is the pickup surface of the residual noise detecting second transducer of the present invention located in that same plane. All three transducers are located on a supporting frame structure.

The second input transducer, however, because it is oriented to transduce acoustic waves in the ear canal cavity, also picks up the cancelling opposing sound waves being generated by the output transducer. These opposing waves are cancelling noise as desired and therefore should not themselves be cancelled. Because the residual input transducer should only provide cancelling of a part of the frequency range due to imperfections in the amplitude and phase response of the first transducer versus the output transducer, the output of the residual second input transducer is filtered. Accordingly, the portion of the electrical output from the second transducer which is due to the opposing sound waves generated by the output transducer is filtered from the portion of the electrical output due to the residual noise to be cancelled.

This invention is an "open air" type device in that an ear muff need not provided, nor is a attenuating ear-cavity-forming foam cushion required. Rather, a non-attenuating open cell foam cushion covers the surface of the composite transducer. When the composite transducer is placed against the ear in use, the foam provides a cushion, windscreen, and spacer between the ear pinna of the user and the rest of the composite transducer assembly of the headphone.

The electrical circuitry of the control unit of the present invention is similar to the circuitry disclosed in the parent Application Ser. No. 07/532,323 except that it has an input for receiving the electrical output from the second input transducer. It therefore drives the diaphragm of the output transducer based on both the noise detected by the first input transducer and also the residual noise detected by the second input transducer.

Additionally, in order the simplify the electronics of the device, the electronics of the present invention merely inverts the incoming noise to generate a cancelling 180° phase shifted acoustic wave into the ear canal. The composite transducer is, however, an "open air" device. Noise to be cancelled therefore travels from the noise source, around the sound-blocking composite transducer, through the foam between the composite transducer and the ear, and into the ear canal. The path of the noise from the noise source, through the electronics, and into ear canal, on the other hand, is a shorter distance. Furthermore, due to the almost instantaneous processing speed of the electronics with respect to the speed of sound, the path from the noise source, through the device, and into the ear canal has a still shorter effective distance when compared to the path of the noise to be cancelled.

The present invention therefore adds a baffle between the noise source and the electronics, around which the noise picked up by the electronics must first travel. The baffle, therefore, increases the distance the noise travels before it is picked up and processed by the electronics. Accordingly, with the use of the baffle, the "open air" device of the present invention is able to utilize simple inverting circuitry and still output cancelling acoustic waves which are 180° out of phase with respect to the noise to be cancelled.

BRIEF DESCRIPTION OF THE DRAWINGS

Other features and objects of the invention will become more readily apparent from the following detailed description when read in conjunction with the accompanying drawings in which.

DESCRIPTION OF THE PREFERRED EMBODIMENT

Figure 1:
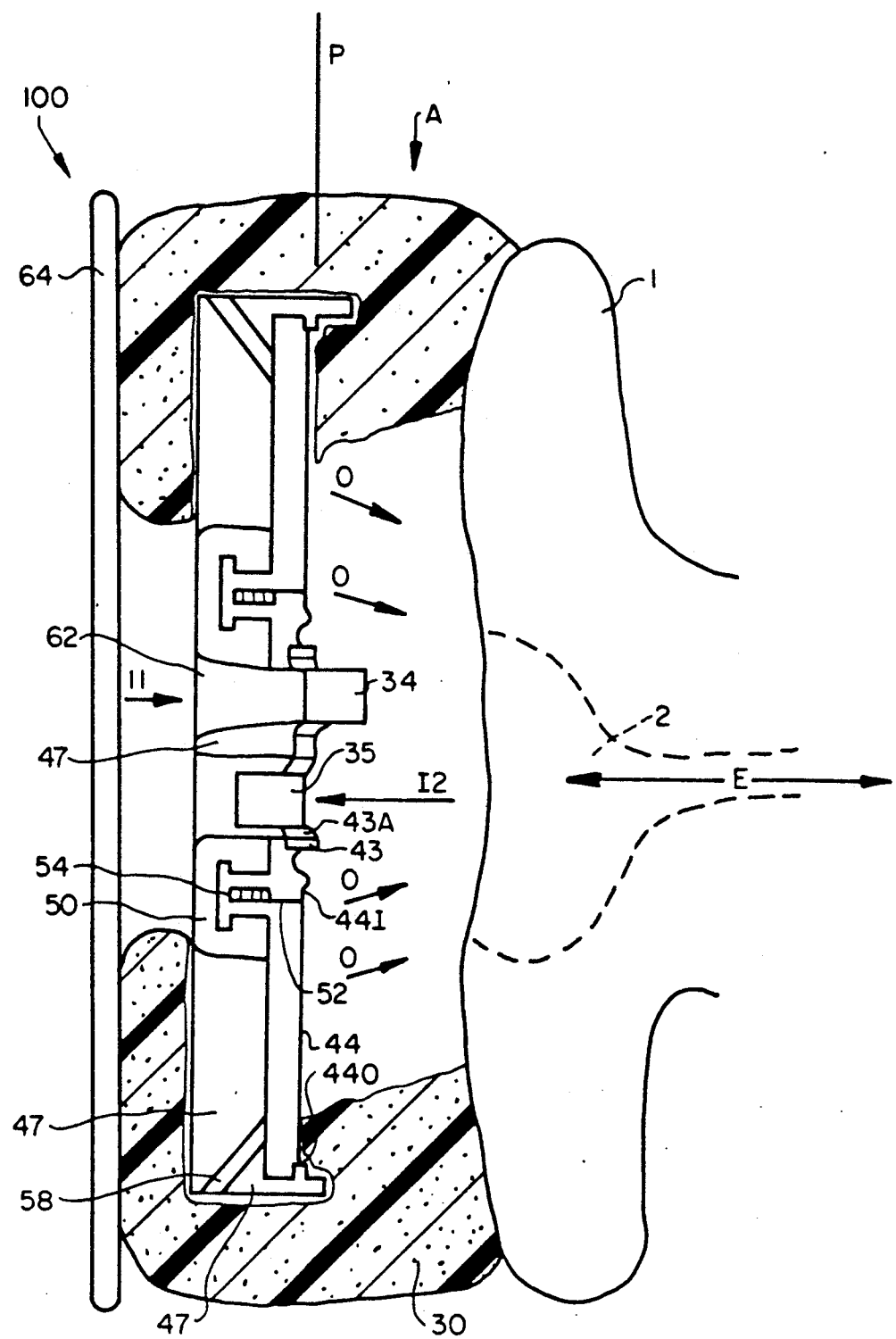
FIG. 1 is side cross sectional view of the composite transducer assembly of the invention located on a use's ear and using electret microphones.

FIG. 1 is side cross sectional view showing the composite transducer assembly 100 of the electroacoustic device when in use on the ear pinna 1 of a user. First input transducer 34 is oriented so that it receives noise sound waves through conical horn 62. Conical horn 62 is provided to avoid standing sound waves of resonances from forming in what would otherwise be a cylindrical tube. The incoming noise sound waves received by the first input transducer 34 are depicted as arrow I1.

Second input transducer 35 is oriented facing in the opposite direction facing ear canal cavity 2 so that it receives residual noise sound waves inside ear canal cavity 2. The acoustic waves propagating from the ear canal are depicted emanating in direction I2. Both the first and second input transducers 34 and 35 are fixed to frame structure 47 so that the surfaces of the input transducers upon which the sound waves are incident lie in substantially the same plane P.

Fixing the input transducers in the same plane is accomplished in the embodiment of FIG. 1 by first securing the input transducers 34 and 35 to a center disc 43 with glue 43A. This glue forms an airtight seal between the ear-facing side of the transducer assembly and the outward-facing side of the transducer assembly. Numerous compounds can be used to fix the transducers to center disc 43. Silicon sealant and epoxy glue have been found to be suitable. Center disc 43 is then fixed to the frame structure 47. Center disc 43 is not required, however, and the input transducers 34 and 35 can be directly fixed to the frame structure 47 without any such center disc 43.

Diaphragm 44 of output transducer 36 is oriented to face inwardly toward ear pinna 1 in the same direction that second input transducer 35 faces. Output transducer 36 therefore produces acoustic waves which propagate in the direction of the ear pinna 1 and ear canal cavity 2 as depicted by arrows O.

Vent ports 58 are provided for equalizing air pressure differences between the ear-facing side of the output transducer diaphragm 44 and the space between diaphragm 44 and frame structure 47 of the composite transducer structure 100. Output transducer 36 is operated by coil windings 54 wound on coil form 52 and an associated magnet structure 50. In the preferred embodiment, a thin profile output transducer is used so that the entire composite transducer assembly has as thin a profile as possible.

The ear-facing side of the composite transducer is provided with a cushion 30. Although this cushion is made of an open cell foam which does not appreciably attenuate acoustic energy, the cushion does function as a wind screen to impede air flow parallel to plane P between diaphragm 44 and the ear canal cavity 2.

The cushion 30 also maintains the composite transducer a distance away from the ear pinna 1 in a desired orientation relative to the ear canal cavity 2. Accordingly, both the first input transducer 34 and the second input transducer 35 are disposed adjacent the ear canal cavity 2 and output transducer diaphragm 44 is disposed substantially perpendicular to the direction E of the ear canal.

Additionally, cushion 30 serves to space a disc-shaped baffle 64 a distance away from the pickup surface of input transducer 34. Baffle 64 serves to impede noise from travelling directly from a source of noise to the input transducer in direction I1. Before noise can reach the pickup surface of the input transducer 34, baffle 64 forces the noise to travel a longer distance around the baffle and through foam 30.

Figure 2:
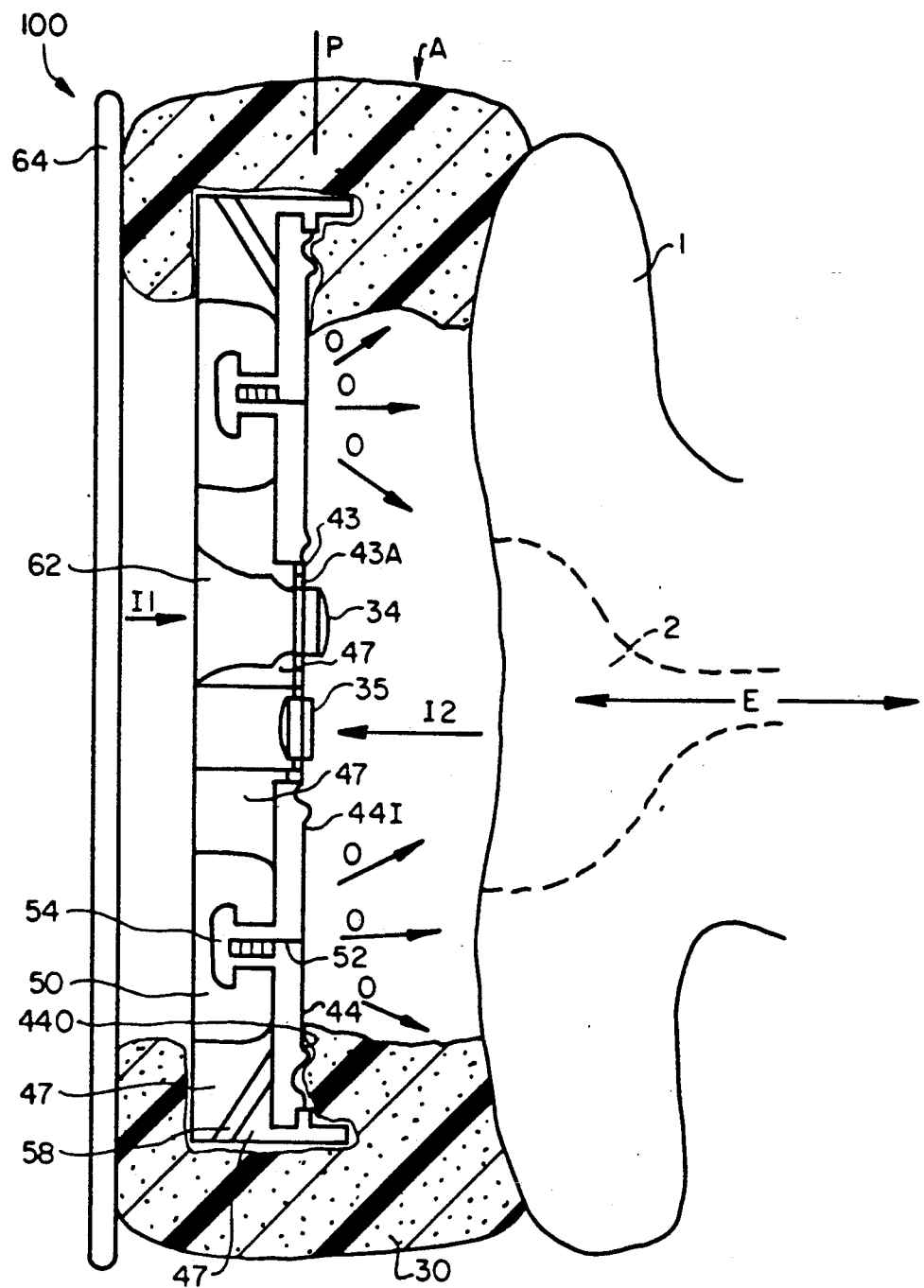
FIG. 2 is a side cross sectional view of the composite transducer, assembly of the invention located on a user's ear and using dynamic microphones.

FIG. 2 is a side cross sectional view of another composite transducer assembly according the present invention. Various types of input and output transducers can be used. FIG. 1 shows the composite transducer assembly using electret type microphones as input transducers whereas FIG. 2 shows dynamic voice coil type microphones as inputs transducers. FIG. 1 shows coil form 52, coil windings 54, and the associated magnet structure 50 located at the inner rim 44I of diaphragm 44, whereas FIG. 2 shows coil form 52, coil windings 54, and the associated magnet structure 50 located halfway between inner rim 44I and outer rim 44O of diaphragm 44. FIG. 1 shows cushion 30 extending only over the outer rim portion of frame structure 47, whereas FIG. 2 shows cushion 30 covering the entire outward-facing side of frame structure 47.

Figure 3:
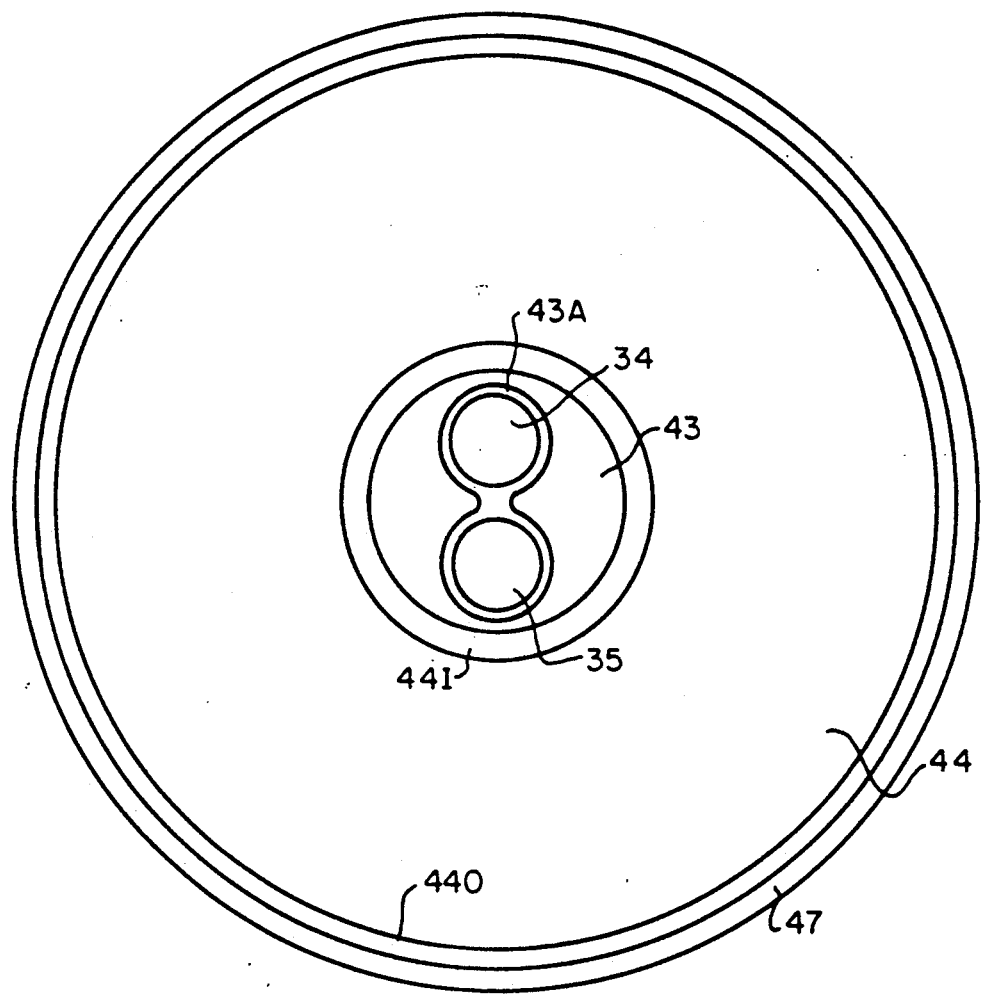
FIG. 3 is a view of the side of the composite transducer which faces towards the ear, shown without the foam cushion and the baffle.

FIG. 3 shows the ear-facing side of the composite transducer assembly with the foam cushion 30 and the baffle 64 removed.

Figure 4:
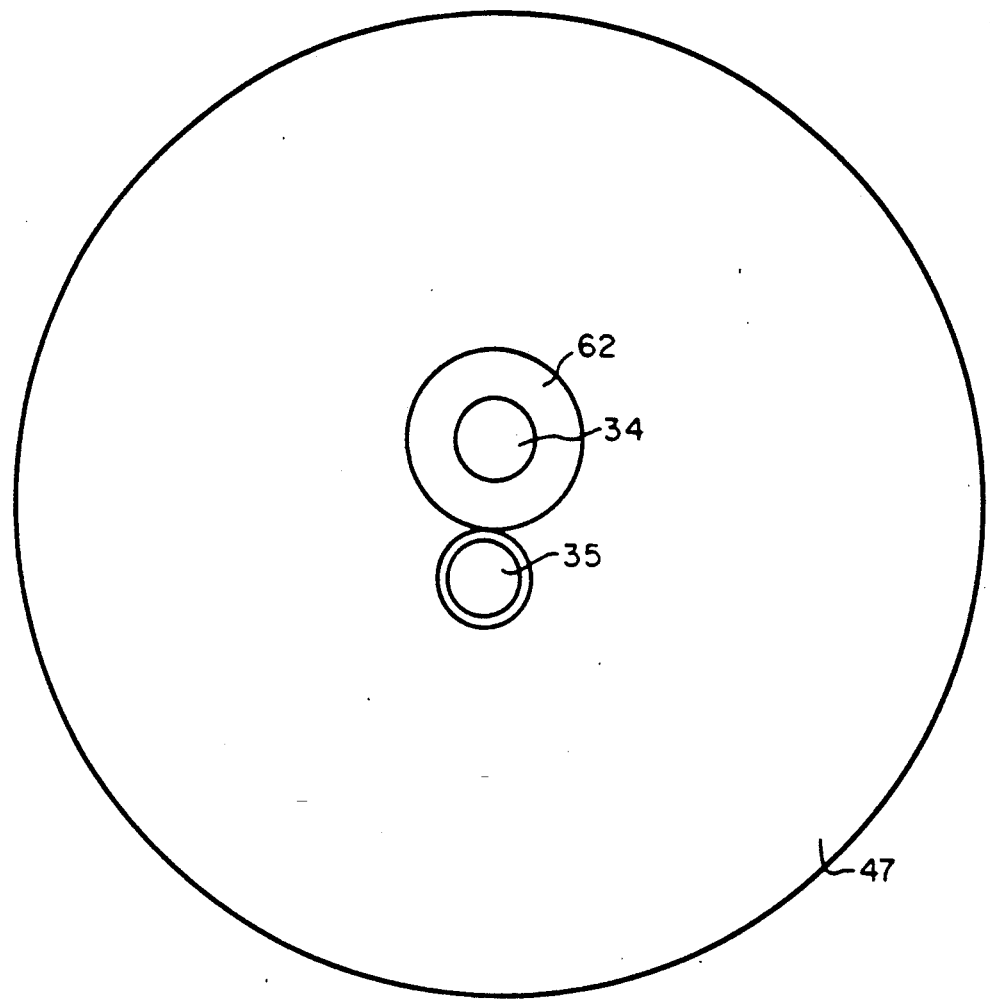
FIG. 4 is a view of the side of the composite transducer which faces outwardly away from the ear, shown without the foam cushion and the baffle.

FIG. 4 shows the outward-facing side of the composite transducer assembly with the foam cushion 30 and the baffle 64 removed.

Figure 5:
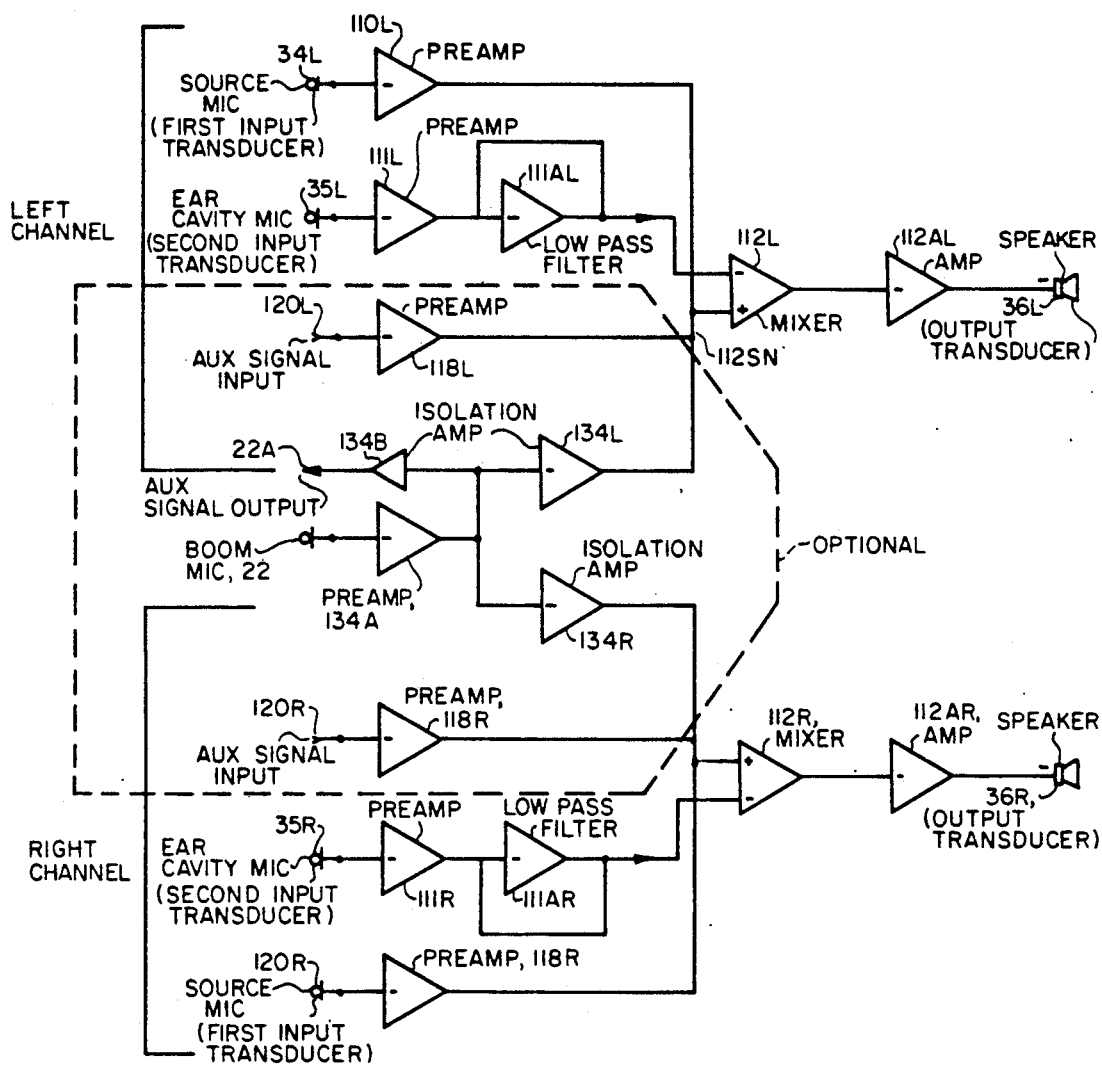
FIG. 5 is a schematic block diagram of a first embodiment of the control circuitry.

FIG. 5 is a schematic block diagram of the circuitry of the control unit according to the presently preferred embodiment. The functioning of this circuitry is much the same as the functioning of the circuitry of FIG. 4 of the parent Application Ser. No. 07/532,323, except for the addition of circuitry associated with the second input transducer 35.

In FIG. 5, both a left channel and a right channel are shown. Because both channels function identically, the operation of only one of the channels is discussed. The "minus sign" in the triangular block symbols denote that the input and output of each triangular block are 180° out of phase.

The first input transducer outputs to a preamplifier 110L which in turn outputs to the positive input of differential mixer amplifier 112L. The output of mixer amplifier 112L is inverted by amplifier 112AL which drives output transducer 36L, here denoted as "Speaker". Due to the 180° phase shift in preamplifier 110L, and the subsequent inversion of amplifier 112AL, the inputs the speaker 36L must be reversed so that the speaker itself introduces an additional 180° phase shift.

Therefore, due to the total 180° phase shift between the first input transducer and the output transducer, due to the very short delay path through the circuitry, due to the reasonably small delay due to ballistics in the output transducer, and due to the coplanar orientation of the input transducer 34L and the output transducer 36L, the opposing sound waves generated by the output transducer 36L cancel the incoming noise which travels past the plane of the first input transducer. This cancellation occurs over a wide frequency of incoming noise signals using very inexpensive operational amplifier circuitry due to the coplanarity of the input and output transducers.

Second input transducer 35L transduces residual noise in the ear canal 2 and outputs a corresponding electrical signal to preamplifier 111L. The output of preamplifier 111L proceeds through low pass filter 111AL and into the negative feedback input of mixer amplifier 112L. Again, due to the reversing of the inputs to speaker 36L, the phase of the acoustic wave incident on the second input transducer 35L is inverted 180° from the phase of the acoustic wave output from speaker 36L.

More specifically in the preferred embodiment, the second input transducer is utilized only to cancel low frequency components of the residual noise detected in the ear canal cavity 2. Low pass filter 111AL therefore prevents the electrical signal corresponding to any high frequency sound in the ear canal cavity from being supplied to the negative feedback input of mixer 112L.

The portion of the schematic block diagram of FIG. 5 surrounded by the dashed line and labelled "optional" is used to establish a communication link with the user of the invention. This portion of the circuitry allows the user to hear himself/herself speak. It also allows the user to listen to intelligence signals input the auxiliary signal input 120L. The type of communication link provided is suitable for use in multiple applications such as in aviation.

The electrical intelligence signal to which the user is to listen is input onto the summing node 112SN via auxiliary signal input 120L and preamplifier 1118L. Because the summing node 112SN is connected to the positive input of mixer 112L, the intelligence signal from the auxiliary signal input is transferred to the speaker 36L for the user to hear.

A boom microphone 22 is also provided for the communication link so that the user can hear himself/herself speaking and so that speech of the user can be transmitted onto the communication link. Boom microphone 22 outputs to preamplifier 134A which outputs to an isolation amplifier 134L which also sums into the summing node 112SN. Accordingly, acoustic waves input into the boom microphone 22 are transferred to speaker 36L so that the user can hear himself/herself speaking.

Next, the communication link provides an auxiliary signal output 22A for outputting to the communication link an electrical signal indicative of the voice of the user. Boom microphone 22 picks up the user's voice and preamplifier 134A outputs the signal to isolation amplifier 134B which drives the corresponding electrical signal out the auxiliary signal output 22A.

Accordingly, the coplanar positioning of the input transducers and output transducer allows the control circuitry to be simple, inexpensive, and realizable in fast analog circuitry which introduces only a negligible phase shift. This analog circuitry is realized with relatively few, inexpensive, readily available monolithic amplifier parts. No special frequency variable delay circuitry is needed to compensate for the differing phase shifts introduced at different noise frequencies which would otherwise be required if the transducers were not oriented in the same plane.

Figure 6:
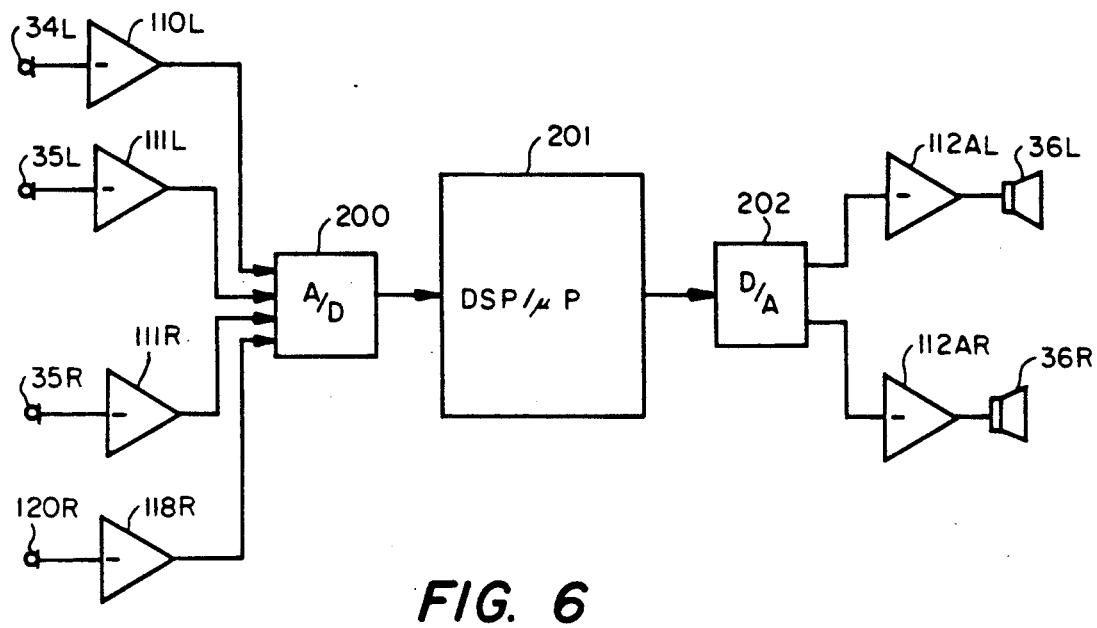
FIG. 6 is a schematic block diagram of a second embodiment of the control circuitry.

FIG. 6 shows a digital alternative to the analog circuit of FIG. 5 without the optional communication interface circuitry.

In the two channels of FIG. 6, both use the same digital signal processor/micro-processor (DSP/$\mu$P) 201. Only the left channel will be explained here because the two channels function identically. First input transducer 34L and second input transducer 35L output their electrical signals to preamplifier circuits 110L and 111L, respectively. A multiplexing sample and hold and analog-to-digital (A/D) converter chip 200 then sequentially digitizes the electrical signals from preamplifiers 110L and 111L. DSP/$\mu$P 201 reads the digitized values and performs any desired filtering, phase shifting, or mixing with other communications signals. The DSP/$\mu$P then writes to demultiplexing digital-to-analog (D/A) converter 202 so that the filtering output is supplied to amplifier 112AL and to output transducer 36L.

Although presently expensive, bulky, and slower than the analog equivalent, the digital circuitry of FIG. 6 can be presently realized with a high speed sample and hold circuit and A/D converter, digital signal processor, and D/A converter. For example, a codec such as the TCM2913 available from Texas Instruments may be used as the A/D converter and the D/A converter. A high speed digital signal processor such as the TMS3210 available from Texas Instruments may be used as the DSP/$\mu$P. Any number of digital filters commonly known in the digital filtering arts could be executed inside DSP/$\mu$P 201. The DSP/$\mu$P 201 may also be programmed with commonly known filters which have known phase delay versus frequency characteristics. Such filters could be used to delay signal components of specific frequencies to compensate for the non-linear phase versus frequency characteristics of the non-ideal input and output transducers.

Figure 7:
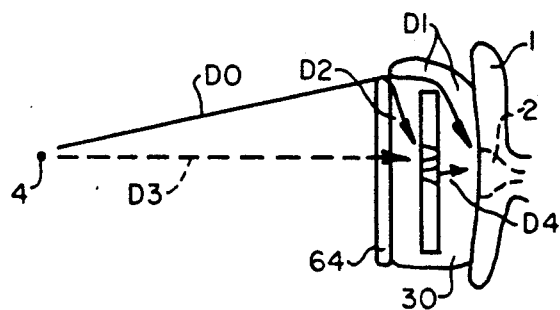
FIG. 7 is a diagram showing the general operation of the baffle of the composite transducer.

FIG. 7 shows how disc-shaped baffle 64 of the present invention serves to allow inverting electronics to supply cancelling acoustic waves into the ear canal which are 180° out of phase with respect to the noise to be cancelled. The path of the noise to be cancelled is traced from noise source 4 by path D0, past baffle 64, through foam 30, around the solid inside portions of the composite transducer, and to ear canal 2 via path D1.

This noise travelling path D0 plus D1 has a first distance.

If there were no baffle 64, the path of sound to the electronics of the composite transducer and from the electronics to ear canal 2 would be that of dashed path D3 and path D4. Because this is a shorter path than that of the path followed by the noise to be cancelled, 180° inverting electronics would output cancelling acoustic waves which may not be 180° out of phase with respect to the noise entering ear canal 2.

Accordingly, baffle 64 is added. With this baffle 64, the path of noise which is converted into cancelling acoustic waves can be lengthened. Due to this lengthening, the phase of the acoustic waves output by the electronics into the ear canal can be brought to be 180° out of phase with respect to a broad frequency range of noise entering the ear canal. In the figure, the path of the noise converted into cancelling acoustic waves is traced from noise source 4 by path D0, around baffle 64, through foam 30 to the electronics by path D2, and from the electronics to ear canal 2 by path D4. Accordingly, it is recognized that the phase of the cancelling acoustic waves can be maintained 180° out of phase with respect to the noise entering the ear canal for a broad range of noise frequencies.

Figure 8:
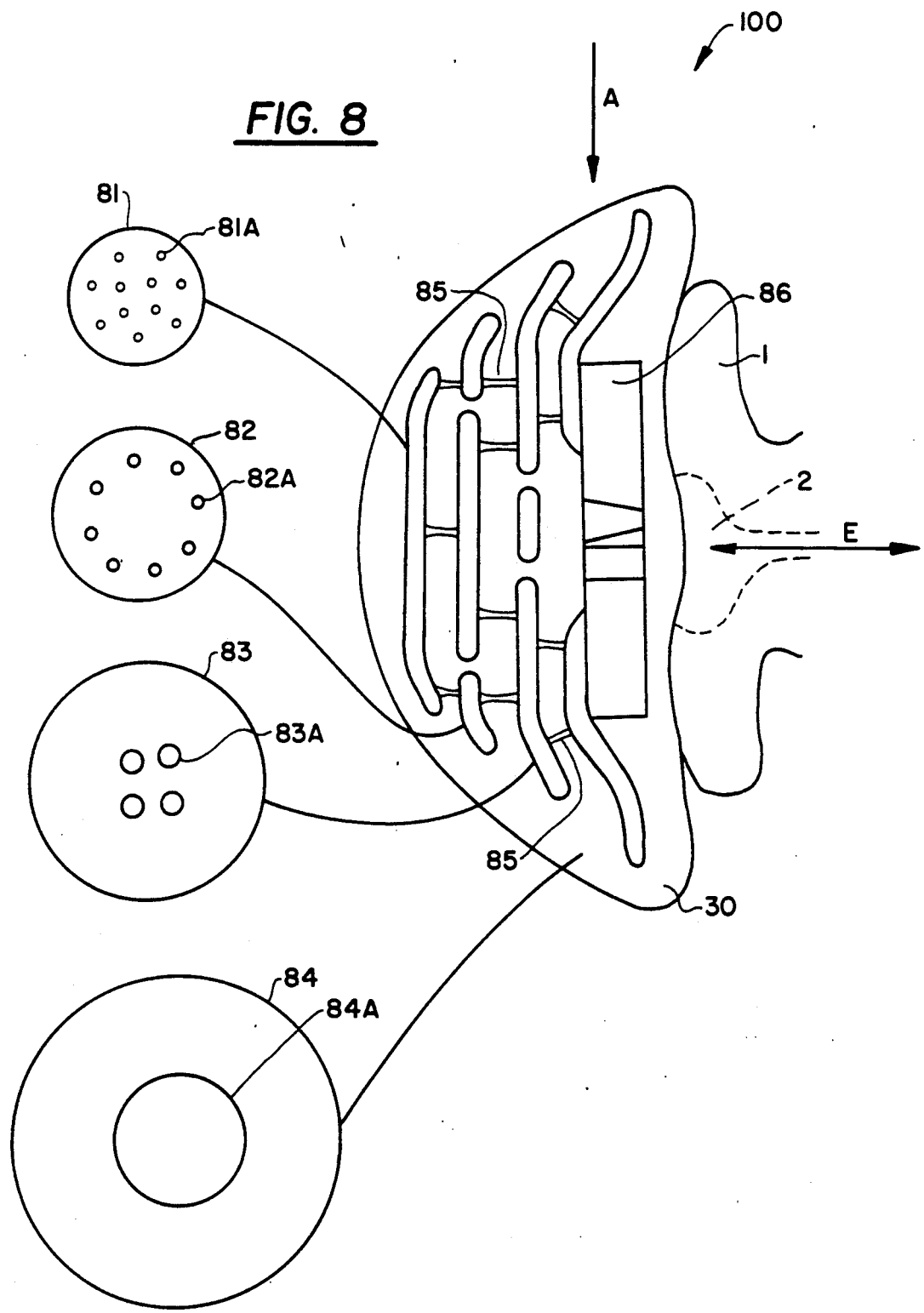
FIG. 8 is a side cross-sectional view of the composite transducer assembly with a multiple baffle acoustic diffuser.

FIG. 8 is a side cross-sectional view of the composite transducer assembly 100 involving a multiple baffle acoustic diffuser. The multiple baffle acoustic diffuser aids the overall effectiveness of the open-air noise cancelling invention by: providing mixing zones for signals entering the diffuser from different directions, absorbing selected frequency components in the incoming noise while allowing others to pass through, and possibly resonate between the discs, providing a means for controlling the distance incoming sound must propagate to reach the input transducers(s) and the ear canal cavity, and providing a type of muffling and back-loading for the output transducer.

Several types of composite transducers 86 can be used in conjunction with the multiple baffle acoustic diffuser. Composite transducer 86 can use either electret microphones as in the composite transducer of FIG. 1, or dynamic microphones as in the composite transducer of FIG. 2. Composite transducer 86 may involve one input transducer as disclosed in Application Ser. No. 07/532,323, or a second input transducer as shown in FIGS. 1 and 2.

The embodiment of the multiple baffle acoustic diffuser shown in FIG. 8 is composed of four thin disc-shaped baffles 81, 82, 83, and 84 of successively larger diameter. These baffles are held a position relative to each other with a number of standoffs 85. These standoffs 85 can be glued to the baffles, snapped into dedicated holes in the baffles, or otherwise fixed to the baffles. Composite transducer 86, baffles 81, 82, 83, and 84, and standoffs 85 are then encased in an open cell, substantially acoustically transparent foam 30 to form the entire composite transducer assembly 100. The open cell foam 30 totally surrounds the baffles and standoffs. In use, the composite transducer assembly 100 fits over the ear pinna 1 of the user to form ear canal cavity 2.

The diffuser is a flexible device in that the design of the baffles can be readily changed to provide different acoustic characteristics through the diffuser. For example, the baffles can be made of a hard plastic if high frequency sounds are desired to pass through the diffuser. In the alternative, if low frequency sounds are to pass through the diffuser and high frequency sounds are to be attenuated, felt baffles can be employed.

In the embodiment of FIG. 8, baffles 81, 82, 83, and 84 include openings 81A, 82A, 83A, and 84A respectively. Openings 81A, 82A, 83A, and 84A are of increasingly larger size. The size, spacing, location, shape, and number of these openings can be varied to control the acoustic properties of the diffuser. If an input transducer is used which faces in direction E away from the ear canal 2, opening 84A is located over the input transducer so that the pickup surface of the input transducer will not be obstructed by baffle 84.

Furthermore, the spacing between baffles can be varied by changing the length of the standoffs. Larger areas between baffles and larger diameter openings provide resonant chambers for lower frequencies, whereas smaller areas and smaller diameter openings provide resonant chambers for higher frequencies.

The outside edges of baffles 81, 82, 83, and 84 have a slight curvature in the direction of composite transducer 86. This curvature serves two principle functions. First, the curvature somewhat obstructs air from blowing past the ear in direction A and from producing undesireable noise inside the diffuser. Second, the curvature serves to provide a means to control the distance the sound must travel before reaching the input transducer in the ear.

Although only selected embodiments of this invention have been described, it will be apparent to a person skilled in the art that various modifications to the structure of the described apparatus and to the details of the described method may be made without departing from the scope of this invention.

I claim:

1. A composite transducer assembly for use in cancelling noise in an ear canal when the composite transducer assembly is in use on an ear, comprising:
   a composite transducer responsive to an opposing sound wave signal to generate an opposing sound wave which propagates from a first side of the composite transducer in a direction into said ear canal, means for generating said opposing sound wave signal to have an amplitude substantially equal to the amplitude of, but substantially 180° out of phase with respect to, said noise in said ear canal; and
   an acoustic diffuser comprising a plurality of substantially planar baffles which are stacked so that each of the baffles lies substantially in a plane which is parallel to the planes of each of the other baffles, the baffles being disposed on a second side of the composite transducer opposite said first side so that each baffle is spaced apart from each other baffle.

2. The composite transducer assembly of claim 1 further comprising an open cell foam which is substantially acoustically transparent and which encases the acoustic diffuser.

3. The composite transducer assembly of claim 1 further comprising a layer of open cell foam which is substantially acoustically transparent and which covers at least said first side of the composite transducer to form a cushion when the composite transducer assembly is in use on said ear.

4. The composite transducer assembly of claim 1 wherein the plane of each of the baffles is substantially perpendicular to said direction into said ear canal.

5. The composite transducer assembly of claim 4 wherein the baffles are substantially disc-shaped.

6. The composite transducer assembly of claim 5 wherein each of the baffles has a diameter, the diameter of each baffle being smaller than the diameter of all other baffles disposed between said each baffle and the composite transducer.

7. The composite transducer assembly of claim 1 wherein the acoustic diffuser further comprises stand-offs which maintain the spacing between the baffles.

8. The composite transducer assembly of claim 1 wherein at least one of the baffles has an opening which leads through the plane of the baffle.

9. The composite transducer assembly of claim 1 wherein at least one of the baffles has a perimeter area which extends in said direction from the plane of said at least one baffle.

10. The composite transducer assembly of claim 1 wherein at least one of said baffles is made of plastic.

11. The composite transducer assembly of claim 1 wherein at least one of said baffles is made of a high-frequency sound absorbent material such as felt.

12. The composite transducer assembly of claim 1 wherein the composite transducer has an input transducer with a pick up surface which is disposed perpendicular to an axis running in said direction into said ear canal, the acoustic diffuser having a substantially washer-shaped baffle disposed perpendicular to said axis, the washer-shaped baffle having a central opening which intersects said axis.

13. The composite transducer assembly of claim 1 wherein at least one of said baffles comprises a disk having a plurality of transverse apertures therethrough.

14. The composite transducer assembly of claim 13 wherein a plurality of said baffles are in the form of a disk with each disk having a pattern of apertures therethrough that differs from the pattern of an adjacent disk.

* * * * *